United States Patent [19]

Fernandez et al.

[11] Patent Number: 5,405,587
[45] Date of Patent: Apr. 11, 1995

[54] APPARATUS FOR STERILIZING AND TRANSPORTING MEDICAL IMPLEMENTS

[76] Inventors: John M. Fernandez, 4518 Azure Ct., Sacramento, Calif. 95864; James R. Colgan, III, 412 W. John St., Carson City, Nev. 89703

[21] Appl. No.: 132,801
[22] Filed: Oct. 7, 1993
[51] Int. Cl.⁶ .......................... A61L 2/00; A61L 2/18
[52] U.S. Cl. .................................... 422/292; 134/186; 134/200; 312/209; 422/300; 422/905
[58] Field of Search .............. 422/292, 300, 905; 134/200, 186, 111; 312/209

[56] References Cited

U.S. PATENT DOCUMENTS

| | | | |
|---|---|---|---|
| 2,480,931 | 9/1949 | Jaeger | 422/300 |
| 2,784,717 | 3/1957 | Thompson . | |
| 3,365,267 | 1/1968 | Kiney et al. | 422/300 X |
| 3,853,329 | 12/1974 | McDonald | 280/47.35 |
| 3,960,224 | 6/1976 | Silvers | 604/245 X |
| 3,963,438 | 6/1976 | Banez | 422/31 |
| 3,974,843 | 8/1976 | Aubert | 134/200 X |
| 3,982,539 | 9/1976 | Muriot | 604/245 X |
| 4,496,522 | 1/1985 | McConnell | 422/300 |
| 4,552,728 | 11/1985 | Taylor | 422/300 |
| 4,688,585 | 8/1987 | Vetter | 134/200 |
| 4,875,696 | 10/1989 | Welch et al. | 280/47.34 |
| 4,989,291 | 2/1991 | Parent | 15/315 |
| 5,040,690 | 8/1991 | van der Schoot | 211/135 |
| 5,090,433 | 2/1992 | Kamaga | 134/200 |
| 5,107,876 | 4/1992 | Ozyjiwsky | 134/200 X |
| 5,152,542 | 10/1992 | DeVoe | 280/47.371 |

FOREIGN PATENT DOCUMENTS 2244919 12/1991 United Kingdom ............... 422/300

OTHER PUBLICATIONS

Olympus Endoscopy System; Urology; 1993; Trade Literature.
Olympys CYF-2, Urology; 1992; Trade Literature.
L-Med Urological Treatment Cabinet; data unknown; Trade Literature.

*Primary Examiner*—Robert J. Warden
*Assistant Examiner*—Krisanne M. Thornton
*Attorney, Agent, or Firm*—John P. O'Banion; John Costello

[57] ABSTRACT

An apparatus (10) for sterilizing and transporting medical implements (52). A rectangular, cabinet-like, support structure (12) surrounds a self-contained sterilization system generally defined by a storage rack (58), a container-like collection vessel (34) and a tube-like fluid transport line (42). Storage rack (58) includes wet wells (46a) and dry wells (46b). Wet wells (46a) are filled with sterilization fluid, and medical implements (52) are immersed therein. Following sterilization, medical implements (52) are placed in dry wells (46b), for storage. Subsequently, the used sterilization fluid in wet wells (46a) can be drained through fluid transport line (42) into collection vessel (34). The apparatus (10) is transportable for easily sterilizing medical implements (52) at different locations.

19 Claims, 4 Drawing Sheets

APPARATUS FOR STERILIZING AND TRANSPORTING MEDICAL IMPLEMENTS

BACKGROUND OF THE INVENTION

1. Field of the Invention

This invention pertains to medical devices generally and, more particularly, to a transportable apparatus for storing and sterilizing medical implements.

2. Description of the Background Art

In an effort to reduce the risk of infection in a clinical environment, the sterilization of medical implements has become a standard practice during the performance of medical procedures. The use of a cystonephroscope during urology procedures represents a typical example of an invasive medical procedure where a risk of infection exists. The cystonephroscope is a device having an ocular portion and a light source for viewing the interior of a patients urinary tract, and an elongate fiber optic cable for placement inside the patient's urinary tract. Because of the invasive usage of the cystonephroscope, it is imperative that any part of the cystonephroscope which contacts the patient's body be thoroughly sterilized.

There have been a number of devices designed for transporting or sterilizing general medical implements, and, in addition, devices which purport to be adaptable for sterilizing cystonephroscopes.

For example, Olympus Corporation Endoscopy System 1993 trade literature discloses a "CYF" cart which provides a station for sterilizing and transporting cystonephroscopes. This cart is fully transportable and employs a large bowl to allow the complete immersion of a cystonephroscope in a sterilization fluid.

U.S. Pat. No. 3,853,329 issued to McDonald on Dec. 10, 1974, discloses a surgical supply cart which allows for the storage and transportation of numerous surgical implements. The entire cart can be loaded with unsterilized implements and can be subjected to a steam sterilization procedure prior to surgery.

A primary drawback with the sterilization carts mentioned above, are their inability to efficiently fluid sterilize a cystonephroscope while using minimal amounts of sterilization fluid. While the Olympus "CYF" cart allows a cystonephroscope to undergo a fluid sterilization procedure, the usage of a bowl as an immersion well requires copious amounts of sterilization fluid to immerse a cystonephroscope, resulting in a significant waste of sterilization fluid. Moreover, by using a bowl to immerse the cystonephroscope, the fiber optic cable portion must be wound up to accommodate the bowl's shape, which requires bending the cable, a condition which is not conducive to a long cable life. Therefore, a need still exists for a sterilization cart which allows for a cystonephroscope to be sterilized while using minimal amounts of sterilization fluid and which allows the fiber optic cable portion of the cystonephroscope to be sterilized while in a fully extended position.

Additionally, a variety of carts have been devised to carry tools or other equipment in other applications unrelated to sterilization:

For example, U.S. Pat. No. 3,960,224 issued to Silvers on Jun. 1, 1976, discloses an apparatus for storing and transporting a precision cut-off weighing apparatus, comprised of a pair of scales designed to precisely weigh volumes of body fluids contained in a bag. The scales are stored and transported in a cabinet mounted on a plurality of caster wheels.

U.S. Pat. No. 2,784,717 issued to Thompson on Mar. 12, 1957, discloses an evacuative suction apparatus for use in connection with medical or dental procedures comprised of a cabinet mounted on caster wheels having an electric vacuum device located therein.

U.S. Pat. No. 3,982,539 issued to Muriot on Sep. 28, 1976, discloses a medical/surgical suction apparatus comprised of a vacuum chamber for depositing body fluids into a collection bag. This device has several wheels and is transportable.

U.S. Pat. No. 5,040,690 issued to van der Schoot on Aug. 20, 1991, discloses a rolling container comprised of a cabinet mounted on caster wheels. The interior of the cabinet has a plurality of shelves for accommodating egg trays.

U.S. Pat. No. 5,152,542 issued to DeVoe on Oct. 6, 1992, discloses a classroom traveler cart for transporting and storing heavy equipment used in a classroom environment. Additionally, this apparatus has a power strip which can be plugged into an adjacent wall outlet for purposes of accommodating electrically powered equipment. A plurality of caster wheels and a guide handle provide adequate means for transporting and guiding the apparatus.

U.S. Pat. No. 4,875,696 issued to Welch et al. on Oct. 24, 1989, discloses a caster direction-locking mechanism for a mobile cart which allows for the casters on a mobile cart to be selectively locked for providing directional maneuverability.

U.S. Pat. No. 4,989,291 issued to Parent on Feb. 5, 1991, discloses a computer servicing cart comprised of a wheeled housing having a rear compartment containing a compressed gas source and a variety of tools and cleaning solutions for servicing computers.

The foregoing references disclose a variety of carts and other devices designed for storing, transporting or sterilizing medical implements and other tools. The devices disclosed in the foregoing references do not provide for the economical fluid sterilization of a cystonephroscope wherein the fiber optic portion of the cystonephroscope can be sterilized in a fully extended position. The present invention accomplishes both of these objectives. Moreover, the present invention allows for the economical fluid sterilization of a variety of other medical implements besides cystonephroscopes.

The foregoing references reflect the state of the art of which the applicant is aware and are tendered with the view toward discharging applicant's acknowledged duty of candor in disclosing information which may be pertinent in the examination of this application. It is respectfully stipulated, however, that none of these patents teach or render obvious, singly or when considered in combination, applicant's claimed invention.

SUMMARY OF THE INVENTION

This invention pertains to an apparatus for transporting and sterilizing medical implements, and is specifically adaptable for usage with a cystonephroscope. The present invention sterilizes medical implements by employing a series of wet wells adapted for receiving a sterilization fluid and a series of dry wells for storing the medical implements following sterilization. The wet wells communicate with a number of containers which serve as a collection means for collecting spent sterilization fluid. A length of tubing serves as a fluid transport means for carrying sterilization fluid by gravity feed between the wet wells and the collection means. Additionally, the tubing may have a stop cock located between the wet wells and the collection means for regulating the flow of sterilization fluid.

The fluid transport means and collection means are contained within a support structure which is preferably cabinet-like in its appearance and function, the cabinet preferably having a plurality of caster wheels for allowing the entire apparatus to be easily transported.

An object of the invention is to provide an apparatus for the transport, storage and sterilization of medical implements.

Another object of the invention is to provide an apparatus having wet wells for sterilizing medical implements and dry wells for storing medical implements prior to, or subsequent to sterilization.

Another object of the invention is to provide an apparatus which has a means for draining spent sterilization fluid from the wet wells.

Another object of the invention is to provide an apparatus which is maneuverable within the confines of a small examination room.

Another object of the invention is to provide an apparatus which allows for the economical usage of sterilization fluid.

Still another object of the invention is to provide a transport, sterilization and storage apparatus for a flexible cystonephroscope, wherein the apparatus includes means for accommodating the flexible fiber optic cable of the cystonephroscope.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 1:
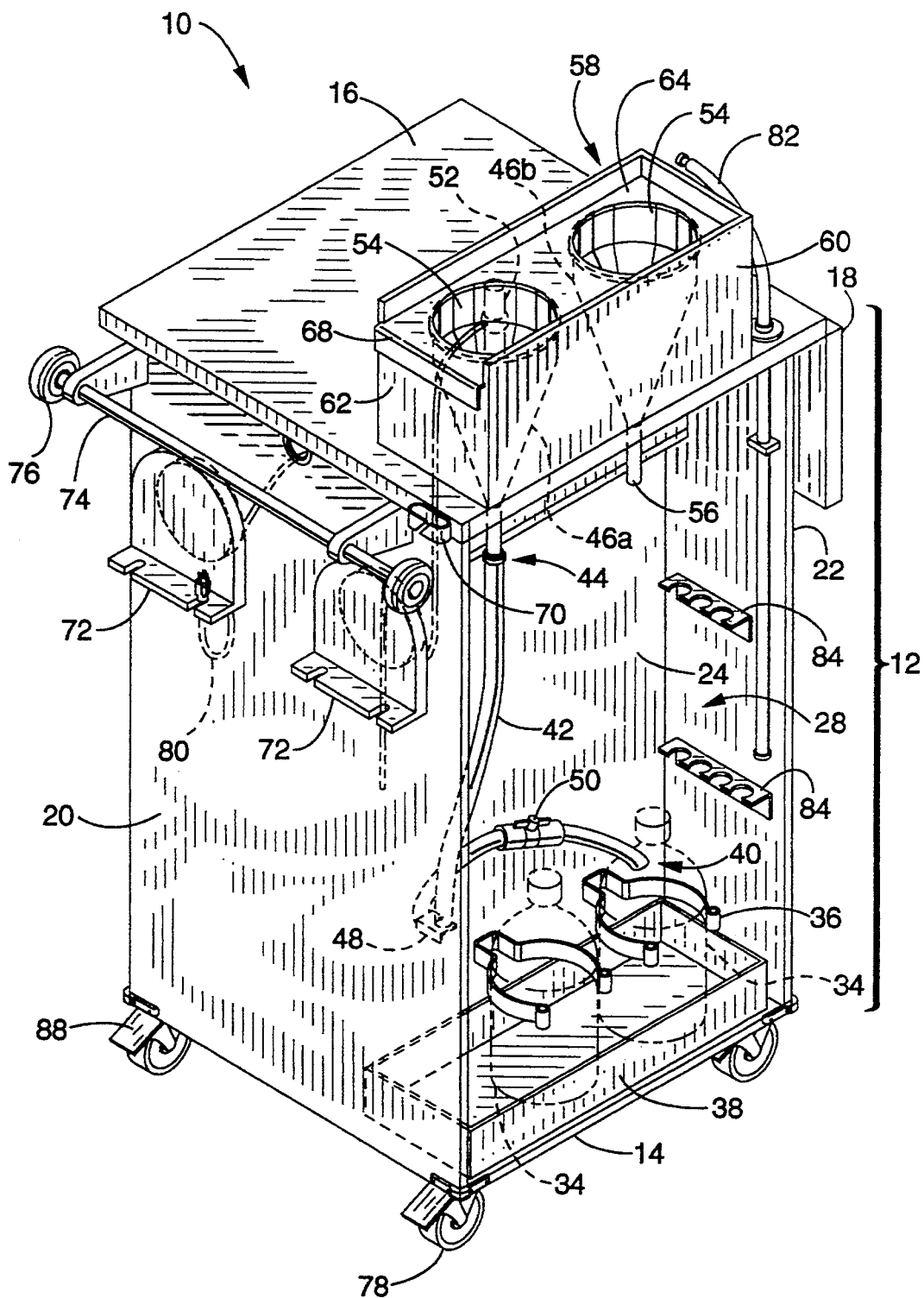
FIG. 1 is a perspective view from the rear of the apparatus of the present invention showing the sterilization means.

Referring more specifically to the drawings, for illustrative purposes the present invention is embodied in the apparatus 10 generally shown in FIG. 1. It will be appreciated that the apparatus 10 may vary as to configuration and as to details of the parts without departing from the basic concepts as disclosed herein.

Figure 2:
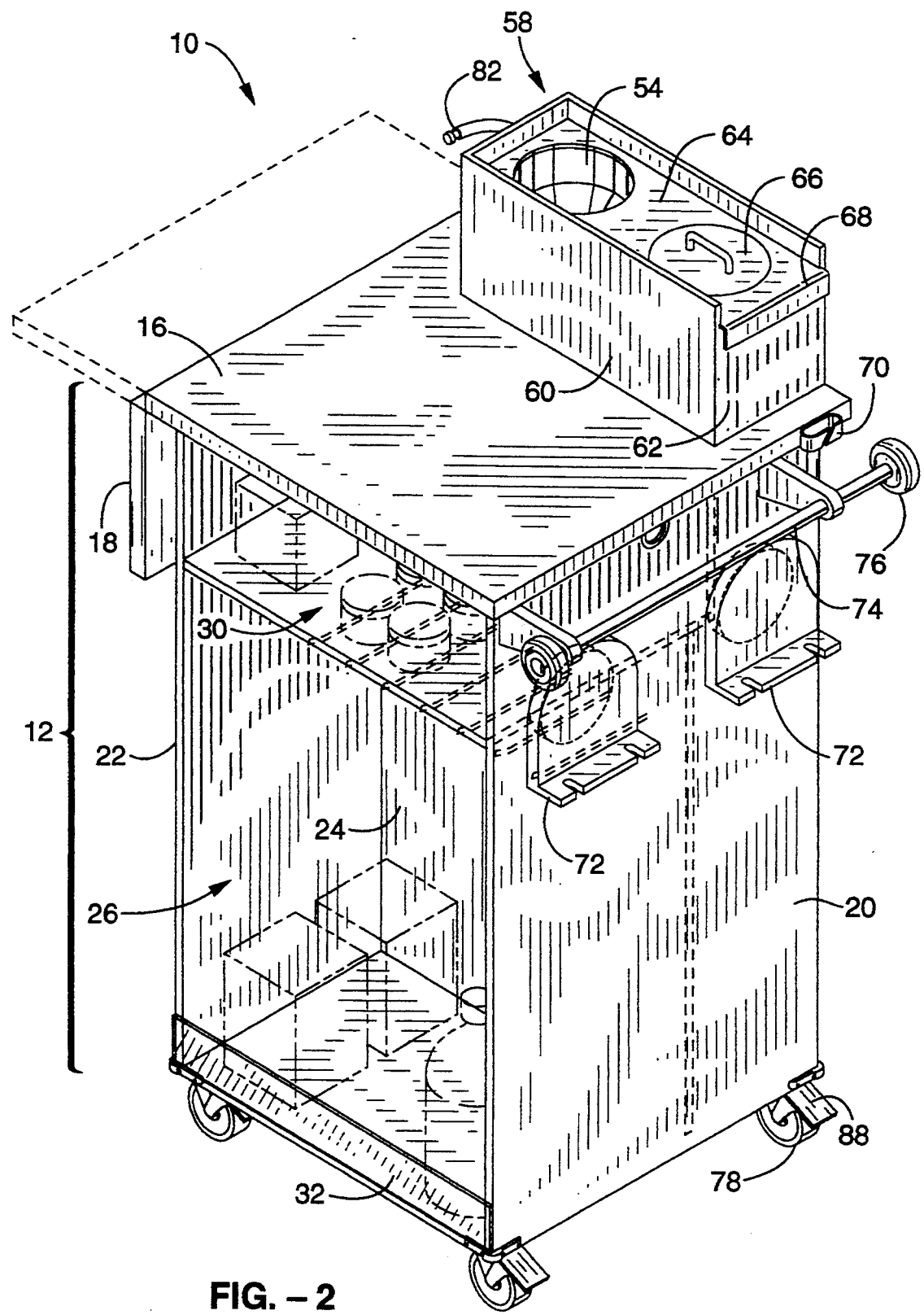
FIG. 2 is a perspective view from the front of the apparatus of FIG. 1.
Figure 3:
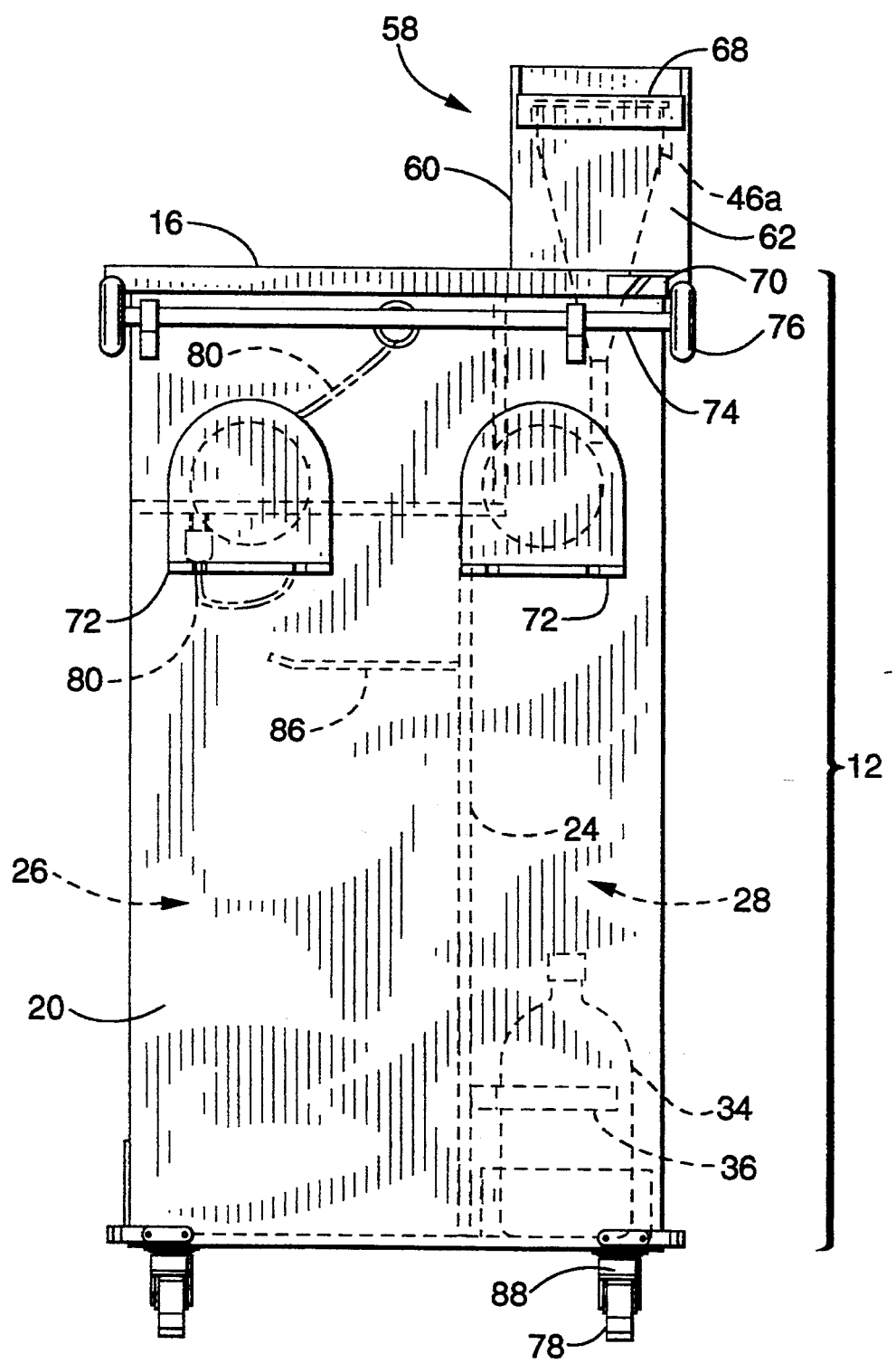
FIG. 3 is a side elevation of the apparatus of the present invention.

Referring to FIG. 1, FIG. 2 and FIG. 3, the apparatus 10 of the present invention includes a support structure 12, which is preferably of a rectangular cabinet-like configuration. To best describe the elements of support structure 12, a three dimensional plane having a vertical "Y" axis and two horizontal "X" and "Z" axes can be used. In the preferred embodiment of the present invention, support structure 12 includes a base 14, a top 16, a pivoting top extension 18 and a pair of sides 20 and 22. Base 14 and top 16 would preferably be disposed along the X-Z plane at opposite ends of sides 20 and 22, which would preferably be disposed in the Y-Z plane. Top 16 and top extension 18 operate as a work surface which in the preferred embodiment can accommodate a sterile gauze barrier. In addition, support structure 12 preferably includes a partition 24 extending in a substantially perpendicular relation in the X-Y plane between sides 20 and 22, as well as between top 16 and base 14. Partition 24 serves to divide support structure 12 into a front compartment 26 and a rear compartment 28.

Referring to FIG. 2, front compartment 26 is shown. In the preferred embodiment, front compartment 26 may be used for the storage of a plurality of medical supplies and thus has a plurality of shelves 30 for containing supplies. In addition to shelves 30, apparatus 10 has a shield 32 running parallel to partition 24 along the front of front compartment 26. Shield 32 further insures that any loose articles in front compartment 26 will be suitably held in place.

Referring to FIG. 1, rear compartment 28 can be more closely examined. Inside of rear compartment 28 is one or more collection means 34 for collecting sterilizing material which, in the preferred embodiment, is a sterilization fluid. Collection means 34 may be any one of a plurality of vessels suitable for receiving and containing spent sterilization fluid. Collection means 34 is held in place by holding means 36. Holding means 36 can be any holding means adaptable to holding collection means 34 in substantially the same position while apparatus 10 is being transported. Here, preferably, holding means 36 is comprised of a spring-like bracket which partially surrounds collection means 34 and allows collection means 34 to be removed and replaced within holding means 36, at will. Collection means 34 also preferably rests in spill tray 38 which serves to capture sterilization fluid which may spill during normal operation.

Collection means 34 is coupled to a first end 40 of a fluid transport means 42. Fluid transport means 42 is coupled at a second end 44 to wet well 46a. A corresponding dry well 46b is positioned adjacent to wet well 46a. Fluid transport means 42 is further coupled to support structure 12 by coupling means 48, which is preferably a bracket suitable for holding fluid transport means 42 in place. Fluid transport means 42 may be any of a plurality of means which can provide a passageway for the gravity flow of sterilization fluid between wet well 46a and collection means 34, but in the preferred embodiment, fluid transport means 42 is a length of tubing suitable for carrying a variety of materials, including sterilization fluid. It is also preferable that if fluid transport means 42 is a length of tubing, that the diameter and length of the tubing be sufficient for accepting a fully extended fiber optic cable from a typical cystonephroscope, or the like. Disposed within fluid transport means 42 is a regulation means 50 which regulates the flow of sterilization fluid between wet well 46a and collection means 34. Regulation means 50 may be any of a plurality of devices capable of selectively restricting the gravity flow of sterilization fluid between wet well 46a and collection means 34 but, in the preferred embodiment, regulation means 50 is a stop cock. By operating regulation means 50, the flow of sterilization fluid may be increased or terminated completely, depending on the requirements of the user.

Following a sterilization procedure, a user may decide that the sterilization fluid has become contaminated or else has reached the end of its useful life. If this is the case, then by operating regulation means 50, the sterilization material can be drained from wet well 46a and collected in collection means 34.

Still referring to FIG. 1, wet wells 46a and dry wells 46b can be more closely examined. Wet wells 46a serve to sterilize medical implements 52 while dry wells 46b serve to store medical implements 52 when they are not in use. Wet wells 46a and dry wells 46b are identical in every respect, except that wet wells 46a are coupled to fluid transport means 42, unlike dry wells 46b. Hence wet wells 46a are readily adaptable to being filled with sterilization fluid, after which a medical implement 52 may be immersed in the fluid to be sterilized. It has been found that the preferable number of wells should be two, wherein one well is a wet well 46a and one well is a dry well 46b, for purposes of having an apparatus 10 which is maneuverable in confined spaces.

Wet and dry wells 46a and 46b have a first opening 54 and a second opening 56. Upon extending vertically downward into rear compartment 28, wet well 46a is coupled at second opening 56 to the second end 44 of fluid transport means 42. Second opening 56 of wet well 46a is preferably adapted to couple easily with second end 44 of fluid transport means 42. Wet and dry wells 46a and 46b may be of any shape, but funnel-like shapes which communicate closely with, and hold medical implements 52 in an immovable position, are preferable. It is also preferable that wet and dry wells 46a and 46b be constructed from a scratch-preventing material such as polyethylene, to avoid scratching or otherwise damaging medical implements 52 stored therein.

For example, apparatus 10 of the present invention is especially adaptable for storing and sterilizing cystonephroscopes which typically have a cylindrical body attached to an elongate, flexible, fiber optic cable which is typically teflon-coated and must be protected. Wet and dry wells 46a and 46b having been constructed from a scratch-resistant material, would avoid damaging any of the delicate or teflon-coated components of the cystonephroscope. Moreover, the flexible fiber optic cable of the cystonephroscope could be fully extended into fluid transport means 42 below wet well 46a, so that the fiber optic cable could contact the sterilization fluid inside fluid transport means 42.

It is important to note that the apparatus 10 of the present invention significantly reduces the volume of sterilization fluid which is required to sterilize medical implements 52. The preferred funnel-like shape of wet well 46a allows for a minimal amount of sterilization fluid to be required to complete a sterilization procedure. For example, in a case where medical implement 52 is a cystonephroscope, previous sterilization devices required from six to eight liters of sterilization fluid to complete a typical sterilization procedure. The apparatus 10 of the present invention requires less that 1 liter of sterilization fluid to complete an identical sterilization procedure involving a cystonephroscope.

Figure 4:
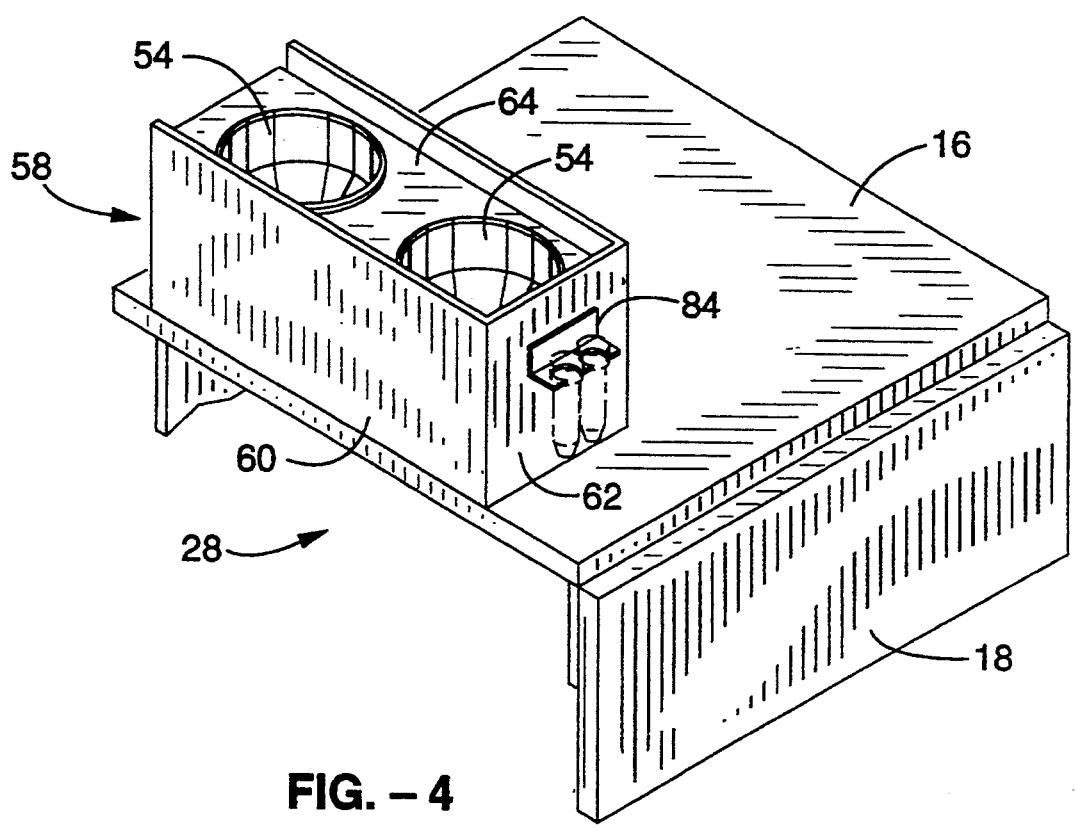
FIG. 4 is a detail view of the storage means of the apparatus shown in FIG. 1, rotated 90 degrees.

Referring additionally to FIG. 2 and FIG. 4, it can be seen that wet and dry wells 46a and 46b respectively, are contained within storage means 58. Storage means 58 may be positioned in any arrangement which allows for the gravity flow of sterilization material between wet well 46a and collection means 34, however storage means 58 is preferably coupled to the rear edge of top 16 above rear compartment 28 and collection means 34.

Storage means 58 is preferably composed of substantially planar sides 60 and 62, deck 64, and cover 66. Deck 64 has holes placed into its surface to accommodate cover 66. Cover 66 communicates closely with deck 64 and thus prevents the loss of fluid or medical implements 52 from the interior of wet well 46a or dry well 46b. Cover 66 is preferably an escutcheon plate having a handle for easy removal. It is also preferable that all components of cover 66 be of a non-metallic, non-reactive material, as it has been found that metal components undesirably catalyze the breakdown of sterilization fluid in wet wells 46a. In an alternate embodiment, cover 66 may be of a character such that when cover 66 is closed upon wet well 46a or dry well 46b, a tight engagement results which, prevents the influx of airborne contaminants from the outside environment.

In addition, deck 64 has at least one rounded edge 68 which functions as an adaption for cystonephroscopes having two or more fiber optic cables, and serves to protect these cables from damage by supplying a rounded surface upon which the cables may rest, while the remainder of the cystonephroscope undergoes a sterilization procedure.

Additionally, support structure 12 has coupled to its sides below rounded edge 68, a plurality of holders 70 and 72 for further securing the free ends of fiber optic cables attached to a cystonephroscope undergoing a sterilization procedure. In addition, handle 74 preferably protrudes outward beyond holders 70 and 72, such that further protection is afforded to any fiber optic cable residing in holders 70 and 72. Handle 74 also preferably has a pair of bumpers 76 attached to its ends, for contacting walls, doors and other obstacles as apparatus 10 is transported through a hospital environment. To facilitate the transport of apparatus 10, a plurality of lockable caster wheels 78 are coupled to the underside of base 14.

Additionally, support structure 12 has an electrical supply means 80 for supplying apparatus 10 with electrical power, should it be needed during a medical procedure. For example, electrical supply means 80 is suitable for supplying alternating current to a light source used in conjunction with a cystonephroscope.

Also coupled to support structure 12 is a slidably extendable intravenous holder 82 for holding an intravenous drip bag. A plurality of syringe holders 84 and hooks 86 are coupled to apparatus 10, to accommodate numerous articles required for medical procedures. For added protection of apparatus 10 of the present invention, a plurality of impact surfaces 88 are coupled near the bottom of support structure 12.

Accordingly, it will be seen that this invention provides an apparatus 10 for sterilizing and transporting medical implements 52. Apparatus 10 allows for the sterilization, storage and transport of medical implements 52 as well as for the storage and transport of accompanying sterilization fluid. The entire apparatus 10 is readily transportable and can therefore, be moved between locations.

Although the description above contains many specificities, these should not be construed as limiting the scope of the invention but as merely providing illustrations of some of the presently preferred embodiments of this invention. Thus the scope of this invention should be determined by the appended claims and their legal equivalents.

I claim:

1. An apparatus for storing and sterilizing medical implements, comprising:

(a) a support structure;

(b) collection means for collecting sterilization fluid, said collection means removably held within said support structure;
(c) storage means for storing and sterilizing medical implements, said storage means coupled to said support structure above said collection means;
(d) a well, said well coupled to said storage means, said well shaped to communicate with a medical implement placed therein, said well having an open first end and an open second end; and
(e) fluid transport means for receiving said medical implement and for transporting sterilization fluid between said well and said collection means, said fluid transport means coupled to an end of said well, said fluid transport means having a regulation means for regulating the passage of said sterilization fluid between said well and said collection means, said regulation means having a first state wherein said sterilization fluid remains in said well and said fluid transport means, and a second state wherein said sterilization fluid flows through said fluid transport means into said collection means.

2. An apparatus as recited in claim 1, wherein said support structure is a rectangular cabinet having substantially planar sides, base and top, said storage means being coupled to said top, said collection means being removably held within said support structure by a holding means, said base coupled to a transportation means for allowing said apparatus to travel.

3. An apparatus as recited in claim 2, wherein said sides of said support structure have a partition located in a substantially perpendicular relation between said sides, said partition defining a front compartment and a rear compartment inside said support structure.

4. An apparatus as recited in claim 3, wherein said wells extend vertically downward into said rear compartment, said rear compartment containing said fluid transport means, said rear compartment further containing said collection means and said holding means.

5. An apparatus as recited in claim 4, wherein said fluid transport means comprises a length of tubing, said regulation means being coupled to said fluid transport means at a point located between said wells and said collection means, said regulation means further being coupled to said support structure by a bracket.

6. An apparatus as recited in claim 5, wherein said front compartment is further divided by a plurality of shelves.

7. An apparatus as recited in claim 6, wherein said transportation means comprises a plurality of lockable caster wheels.

8. An apparatus as recited in claim 7, wherein said collection means is disposed within a spill tray.

9. An apparatus as recited in claim 8, wherein said support structure has an electrical supply means for supplying alternating current to said apparatus, said support structure further including fiber optic cable holders, syringe holders and a slidably extendable intravenous holder coupled thereto.

10. A transportable sterilizing apparatus, comprising:
(a) a support structure, said support structure having a base, a top and a plurality of sides extending between said base and said top;
(b) collection means for collecting sterilization fluid;
(c) holding means for removably holding said collection means in place, said holding means coupled to said support structure;
(d) storage means for storing and sterilizing medical implements, said storage means coupled to said top of said support structure;
(e) at least one wet well, said wet well coupled to said storage means, said wet well having an open first end and an open second end;
(f) at least one dry well, said dry well coupled to said storage means; and
(g) fluid transport means for receiving a medical implement and for transporting sterilization fluid between said wet well and said collection means, said fluid transport means coupled to an end of said wet well, said fluid transport means having a regulation means for regulating the passage of said sterilization fluid between said wet well and said collection means, said regulation means having a first state wherein said sterilization fluid remains in said wet well and said fluid transport means, and a second state wherein said sterilization fluid flows through said fluid transport means into said collection means.

11. An apparatus as recited in claim 10, wherein said support structure is a rectangular cabinet having substantially planar sides, base and top, said base coupled to a transportation means for allowing said apparatus to travel.

12. An apparatus as recited in claim 11, wherein said sides of said support structure have a partition located in a substantially perpendicular relation between said sides, said partition defining a front compartment and a rear compartment inside said support structure.

13. An apparatus as recited in claim 12, wherein said wet well and said dry well extend vertically downward into said rear compartment, said wet well further being coupled to said fluid transport means, said rear compartment containing said fluid transport means, said collection means and said holding means.

14. An apparatus as recited in claim 13, wherein said fluid transport means comprises a length of tubing, said regulation means being coupled to said fluid transport means at a point located between said wet well and said collection means, said regulation means further being coupled to said support structure by a bracket.

15. An apparatus as recited in claim 14, wherein said front compartment is further divided by a plurality of shelves, said front compartment including a plurality of hooks.

16. An apparatus as recited in claim 15, wherein said transportation means comprises a plurality of lockable caster wheels.

17. An apparatus as recited in claim 16, wherein said collection means is disposed within a spill tray.

18. An apparatus as recited in claim 17, wherein said support structure has an electrical supply means for supplying alternating current to said apparatus, said support structure further including fiber optics cable holders, syringe holders and a slidably extendable intravenous holder coupled thereto.

19. An apparatus for storing and sterilizing cystonephroscopes, comprising:
(a) a support structure, said support structure having a base, a top, a first side, a second side, a partition, a rear compartment and a front compartment;
(b) collection means for collecting sterilization fluid, said collection means being held inside said rear compartment of said support structure;
(c) holding means for removably holding said collection means in place, said holding means coupled to said support structure inside said rear compartment;

(d) storage means for storing and sterilizing said medical implements, said storage means coupled to said top of said support structure;

(e) a wet well, said wet well coupled to said storage means, said wet well having an open first end and an open second end;

(f) a dry well, said dry well coupled to said storage means;

(g) fluid transport means for transporting sterilization fluid between said wet well and said collection means, said fluid transport means coupled to an end of said wet well, said fluid transport means having a regulation means for regulating the passage of said materials between said wet well and said collection means, said regulation means having a first state wherein said sterilization fluid remains in said wet well and said fluid transport means, and a second state wherein said sterilization fluid flows through said fluid transport means into said collection means; and (h) transportation means for transporting said apparatus between locations, said transportation means coupled to said base.

* * * * *